United States Patent

Bailey

[11] Patent Number: 5,607,430
[45] Date of Patent: Mar. 4, 1997

[54] BONE STABILIZATION IMPLANT HAVING A BONE PLATE PORTION WITH INTEGRAL CABLE CLAMPING MEANS

[75] Inventor: Kirk J. Bailey, Andover, N.J.

[73] Assignee: Biomet, Inc., Warsaw, Ind.

[21] Appl. No.: 519,852

[22] Filed: Aug. 25, 1995

[51] Int. Cl.⁶ .................................................. A61B 17/56
[52] U.S. Cl. ................................. 606/74; 606/60; 606/72
[58] Field of Search ................................. 606/65, 66, 67, 606/68, 69, 70, 71, 72, 73, 74

[56] References Cited

U.S. PATENT DOCUMENTS

| | | |
|---|---|---|
| 2,307,216 | 1/1943 | Graham . |
| 2,612,159 | 9/1952 | Collison ................................. 606/67 |
| 4,269,180 | 5/1981 | Dall et al. . |
| 4,790,303 | 12/1988 | Steffee . |
| 4,889,110 | 12/1989 | Galline et al. . |
| 5,190,545 | 3/1993 | Corsi et al. ............................... 606/72 |
| 5,250,048 | 10/1993 | Gundolf . |
| 5,324,291 | 6/1994 | Ries et al. . |
| 5,415,658 | 5/1995 | Kilpela et al. . |

FOREIGN PATENT DOCUMENTS 2257913   8/1995   United Kingdom .

OTHER PUBLICATIONS

Howmedica—A division of Pfizer Hospital Products Group, Inc.; The Dall–Miles Trochanter Cable Grip System; 12 pages; Pub. 1989.
Howmedica—A Division of Pfizer Hospital Products Group, Inc.; Dall–Miles Cable Grip System; 4 pages; Pub. 1993, 95.

*Primary Examiner*—Micheal Powell Buiz
*Assistant Examiner*—Mark S. Leonardo
*Attorney, Agent, or Firm*—Liell & McNeil

[57] ABSTRACT

A bone stabilization implant comprises a single piece of material machined to include a bone plate portion having a length with a center line, a bone contact surface and an outer surface. The bone plate portion has a plurality of openings extending through the outer surface and the bone contact surface and are located at positions along the length of material. The openings are sized to receive a conventional bone screw. The outer surface is machined to include a plurality of integral bosses positioned at locations along the length. Each of the bosses has crimping surfaces and a pair of holes therethrough that are sized to receive cable. Each of the bosses is deformable to clamp cable received in the pair of holes when the crimping surfaces are crimped. The integration of the bosses with the underlying bone plate portion better facilitates handling of the implant during implantation procedures and substantially reduces the breakage and wear problems associated with prior art bone stabilization implants.

26 Claims, 4 Drawing Sheets

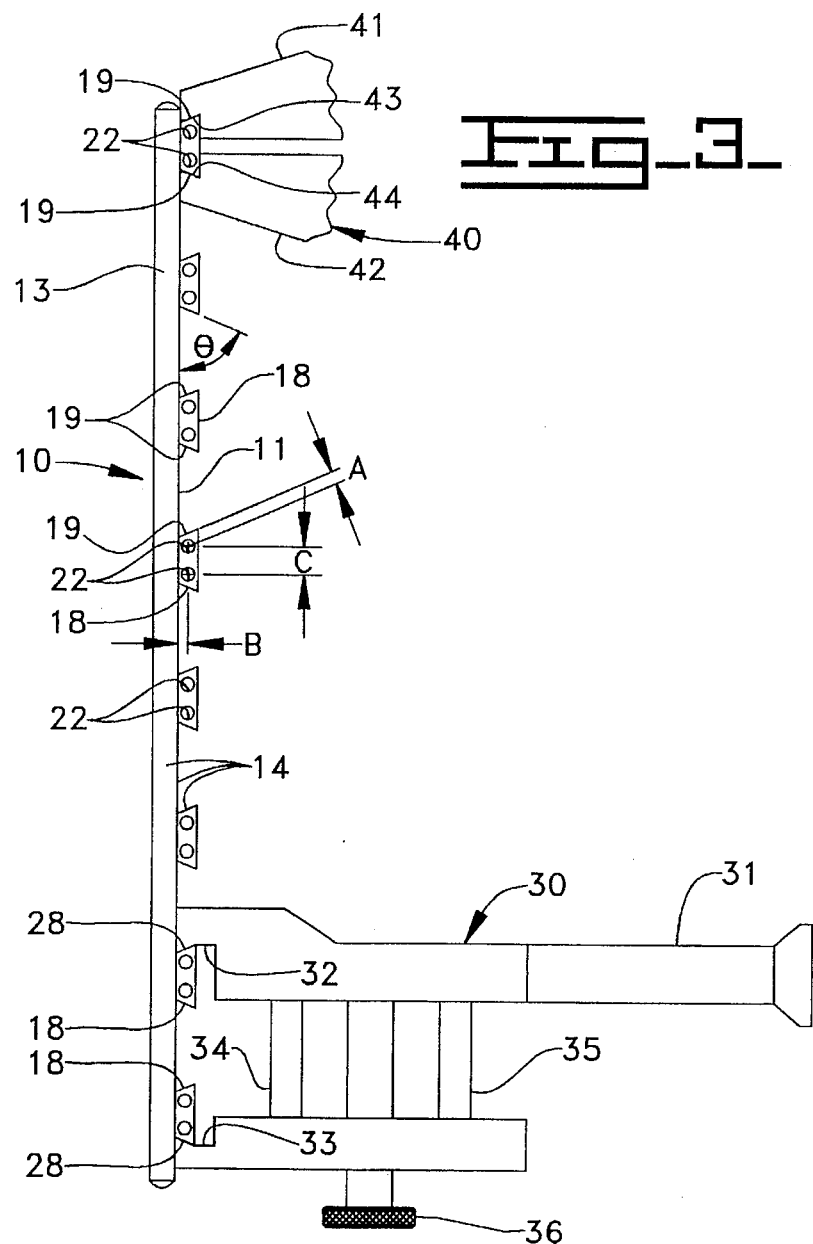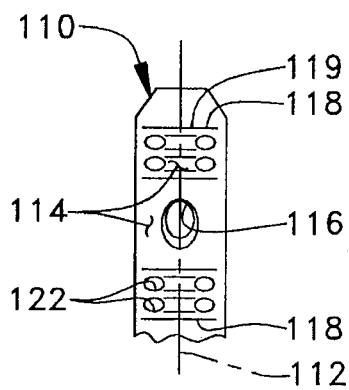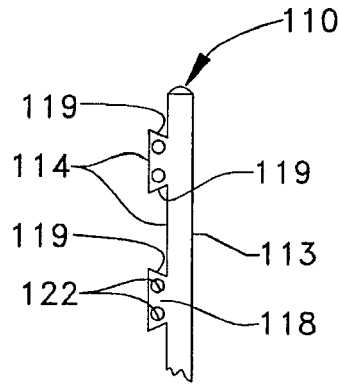

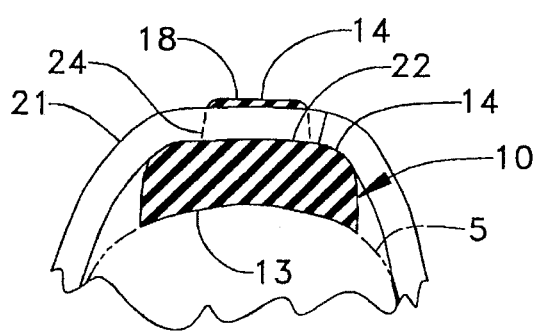
Fig_6_
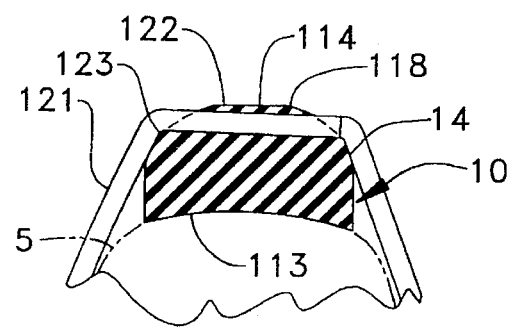
Fig_7_
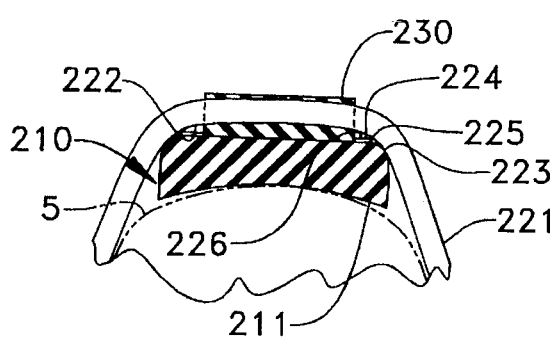
Fig_8_
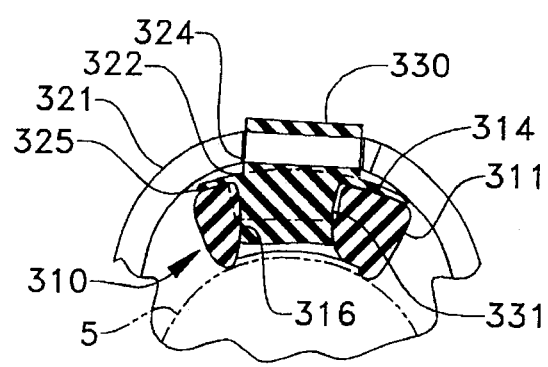
Fig_9_

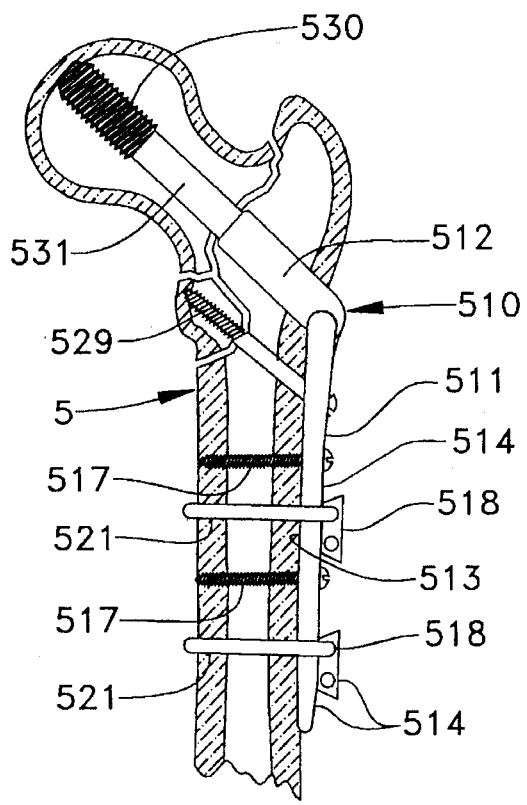
Fig_10_
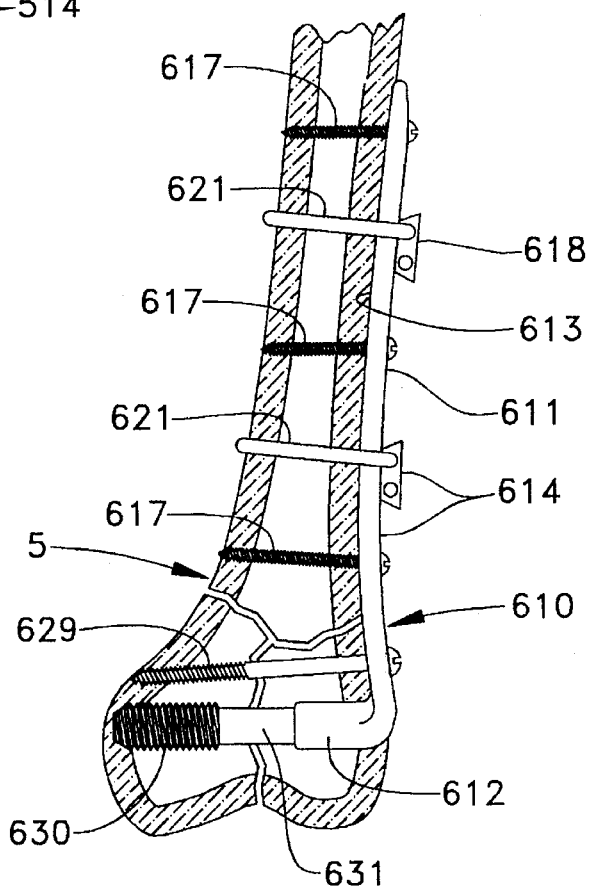
Fig_11_

BONE STABILIZATION IMPLANT HAVING A BONE PLATE PORTION WITH INTEGRAL CABLE CLAMPING MEANS

BACKGROUND OF THE INVENTION

This invention relates generally to bone stabilization implants, and more particularly to bone stabilization implants having a bone plate portion with integral cable clamping means.

In many bone stabilization procedures, particularly those involving elderly patients, it is necessary to attach a bone plate to the patient's bone in order to stabilize the bone, aid in mending a fracture and add strength to an otherwise weakened bone. Although it is usually most desirable to employ the use of bone screws to secure the plate to the patient's bone., it is sometimes necessary to utilize cable to secure the plate to the bone where bone screws, for one reason or another, are unsuitable or undesirable. Such a situation often occurs when obstacles are present or the bone has insufficient material to satisfactorily secure a bone screw or for one of a myriad of other reasons known in the art which render the use of cables more desirable than bone screws.

In one bone stabilization implant of the prior art, bands of metal are used to secure the bone plate portion to the bone. In another prior art bone stabilization implant, separate crimp sleeves are received in machined troughs made in the bone plate portion of the implant. Wire cable is then wrapped around the bone and its ends which are received in the crimp sleeves. In still another prior art bone stabilization implant, separate specially shaped grommets are received in the screw holes of the bone plate portion of the implant. The grommets include crimp sleeves which receive the ends of a cable being utilized to secure the implant to the bone. Unfortunately, all of these prior art devices suffer, to one extent or another, from problems associated with micro motion, unnecessary stressing of the cable or band and unnecessary weakening of the bone plate portion itself.

Micro motion has the potential to occur whenever two metal parts have the potential to move with respect to one another. This micro motion is very undesirable for several reasons: 1) Micro motion causes wear that releases metal fragments into the tissue of the patient potentially causing undesirable side effects; 2) the same wear produced by the micro motion tends to weaken the cable or band securing the bone plate to the bone creating the eventual likelihood of breakage; and 3) wear also tends to weaken the bone plate itself. Micro motion is primarily attributed to the fact that prior art devices utilize a separate crimping device that is held in place against the bone plate portion of the implant only by the tension in the cable or band. Any potential advancement in the art that would substantially eliminate the possibility of this micro motion would lessen the undesirable likelihood faced by many implant patients of having to undergo the second implant operation in order to repair or replace portions of a broken or weakened implant.

Although breakage in a cable can occur due to the micro motion discussed above, it is more often the result of unnecessary stresses on certain portions of the cable due to the structural contours of the assembled bone stabilization implant. In other words, the cable does not rest on a smooth continuous surface in prior art devices, instead the cable is highly stressed in locations where it must round relatively tight corners or otherwise come in contact with a protruding corner. Any advance in the art which aids in uniformly distributing the stress in the cable or band will also help to eliminate the likelihood that some implant patients will have to return to undergo a repair or replacement of their bone stabilization implant.

Another undesirable feature of certain prior art bone stabilization implants utilizing a trough to receive a crimp sleeve, is the fact that the bone plate portion is weakened in that area where a trough is located simply because of the reduction in thickness of the bone plate portion. In other words, a bone stabilization implant having troughs must be made thicker in order to provide the same strength as a bone plate portion having substantially uniform thickness.

Still another undesirable feature of prior art devices is the difficulty encountered when the device is actually implanted. These problems occur both because the prior art devices are more cumbersome to use due to the necessity of manipulating several small and separated crimp sleeves and grommets, as well as the difficulty of manipulating the bone plate portion itself into a desired position. This latter problem occurs primarily because prior art devices lack any good clamping surfaces which would allow a tool to grip the bone stabilization implant to aid in maneuvering it into position during an implant procedure. Prior art devices typically must be manipulated using extra hands and fingers crowding the implant area with attempts to grasp and hold the rounded surfaces typically prevalent on bone stabilization implants.

The present invention is directed to overcoming these and other problems associated with prior art bone stabilization implants.

SUMMARY OF THE INVENTION

The present invention responds to the problems associated with the prior art by providing a bone stabilization implant comprising a single piece of material cast and/or machined to include a bone plate portion having a length with a center line, a bone contact surface and an outer surface. The bone plate portion has a plurality of openings extending through the outer surface and the bone contact surface and positioned at locations along the length. The openings are sized to receive bone screws. The outer surface is machined to include a plurality of bosses positioned at locations along the length. Each of the bosses has crimping surfaces and a pair of holes therethrough that are sized to receive cable. Each of the bosses is deformable to clamp cable received in the pair of holes when the crimping surfaces are crimped. This integrated structure substantially eliminates the micro motion problems associated with the prior art.

In another embodiment of the present invention, a bone stabilization implant for attachment to a bone comprises at least one bone screw, at least one length of cable having two ends, and a single piece of material cast and/or machined to include a bone plate portion having a length with a center line, a bone contact surface and an outer surface. Like the previous embodiment, the bone plate portion has a plurality of openings extending through the outer surface and the bone contact surface that are positioned at locations along the length. The openings are sized to receive the at least one bone screw. Also included are a plurality of bosses positioned at locations along the length, which need not necessarily be integral with the underlying bone plate portion as in the previous embodiment. Each of the bosses has crimping surfaces and a pair of holes therethrough that are sized to receive cable. Also, each of the bosses is deformable to clamp cable received in the pair of holes when the crimping surfaces are crimped. Finally, in this embodiment, each of the pair of holes through the bosses are positioned, and a portion of the outer surface is contoured, to provide a continuous cable contact surface when the ends of the cable are received in the pair of holes. This aspect of the present invention aids in uniformly distributing stress in the cable and substantially eliminating cable breakage problems that occur in the prior art.

One object of the present invention is to substantially reduce the problems associated with micro motion of various parts of a bone stabilization implant.

Another object of the present invention is to more evenly distribute stresses in the cable in order to reduce breakage problems.

Still another object of the present invention is to provide a bone stabilization implant which is less cumbersome to assemble and easier to manipulate during an implantation procedure.

Another object of the present invention is to provide an improved bone stabilization implant.

BRIEF DESCRIPTION OF THE DRAWINGS

FIG. 3 is a side elevational view of a bone stabilization implant of the type shown in FIGS. 1 and 2.

FIG. 4 is a partial top elevational view of a bone stabilization implant according to another embodiment of the present invention.

FIG. 5 is a partial side elevational view of the bone stabilization implant shown in FIG. 4.

FIG. 6 is an enlarged sectioned end view of a bone stabilization implant of the type shown in FIGS. 1–3.

FIG. 7 is a sectioned end view of a bone stabilization implant of the type illustrated in FIGS. 4 and 5.

FIG. 8 is a sectioned end view of a bone stabilization implant according to one prior art device.

FIG. 9 is a sectioned end view of a bone stabilization implant according to another prior art device.

FIG. 10 is a side view of a compression hip screw system according to another embodiment of the present invention.

FIG. 11 is a side view of a supracondylar screw/side plate implant according to still another embodiment of the present invention.

DETAILED DESCRIPTION OF THE PREFERRED EMBODIMENTS

Figure 1:
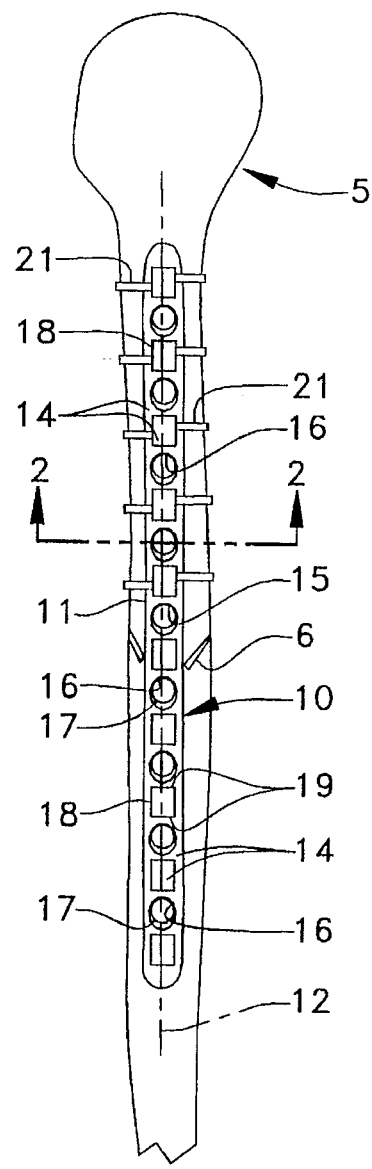
FIG. 1 is a top elevational view of a bone stabilization implant according to the present invention attached to a fractured bone.
Figure 2:
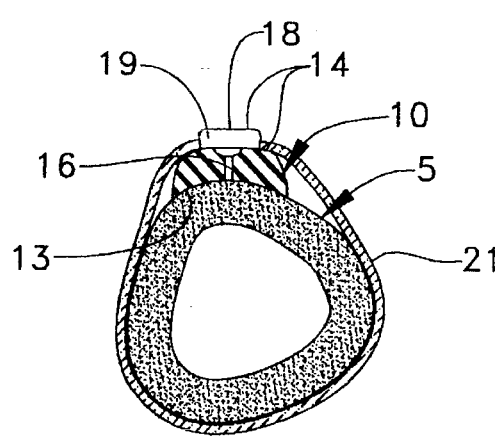
FIG. 2 is a sectioned end view of the bone and bone stabilization implant shown in FIG. 1 taken along section lines 2—2.

Referring now to FIGS. 1 and 2, a bone stabilization implant 10 according to one embodiment of the present invention is shown secured to a fractured bone 5 via bone screws 17 and cable 21. Implant 10 comprises a bone plate 11 having a length with a center line 12, a bone contact surface 13, and an outer surface 14. Bone plate 11 could be cast but is preferably machined from a single solid piece of an implantable metallic surgical alloy, such as stainless steel, titanium alloys or cobalt chrome Molybdenum. Bone plate 11 includes a plurality of openings 15, 16 extending through the outer surface 14 and the bone contact surface 13. A majority of the openings 16 are compression screw holes of a type known in the art. Opening 15 is a neutral hole and is normally positioned closely adjacent the bone fracture 6 of bone 5. In such a way, bone screws 17 received in compression screw openings 16 serve to force fracture 6 together when the screws are threaded into the bone in a manner known in the art.

Outer surface 14 of plate 11 is machined to include a plurality of bosses 18 positioned at locations along the length of the plate. Each of the bosses has a pair of crimping surfaces 19 and a pair of holes therethrough (see FIG. 3). The pair of holes are sized to receive cable, which is typically on the order of 5 millimeters in diameter. Each of the bosses is deformable to clamp cable 21 received in the pair of holes 22 when crimping surfaces 19 are crimped using an appropriate tool. Those skilled in the art will appreciate that cable 21 is fastened to bosses 18 in a conventional manner by inserting one end of the cable under the bone and having both ends of the cable received in the holes of the boss. The cable is then tensioned in order to provide the needed pressure to secure the plate 11 to the bone and then the crimping surfaces 19 are crimped in a conventional manner. Afterwards, the excess cable is trimmed away.

Referring now to FIG. 3, several subtle but key features of the applicant's invention are shown. The upper most boss 18 on bone plate 11 is shown with a pair of crimping pliers 40 in a position to crimp crimping surfaces 19. Crimping device 40 is a type known in the art having a pair of jaws 41 and 42, which include crimping protrusions 42 and 43. These protrusions cause boss 18 and openings 22 to deform in order to clamp the ends of cable received in the openings.

For illustration purposes, the lower two bosses 18 can be considered to include gripping surfaces 28 which facilitate the attachment of a holding device 30. Holding device 30 includes a handle 31, a pair of jaws 32 and 33 that may move with respect to one another utilizing guides 34 and 35. An adjustment screw 36 allows jaws 32 and 33 to clamp onto gripping surfaces 28. As can be seen, gripping surfaces 28 are positioned away from a majority of outer surface 10 in order to provide the exposure necessary to attach a manipulation device, such as holding device 30. Without this ability, the physician or other health care provider is left with manipulating the plate directly by hand or using general instruments during an implantation procedure. The inclusion of gripping surfaces 28, which in this case are identical to crimping surfaces 19, allows the plate 11 to be more easily and securely manipulated during the actual implantation procedure.

It has been found that several dimensions relating openings 22 to the exposed surfaces of bosses 18 are necessary in order to obtain the best possible clamping action when the boss is crimped. Dimension A, which is the distance separating crimping surface 19 from the edge of hole 22 is preferably on the order of about twenty-five thousandths of an inch (0.025"). Likewise, Dimension B, which is the distance between the surface of hole 22 and top surface 27 of the boss 18 is also preferably on the order of about twenty-five thousandths of an inch (0.025"). Finally, the best possible performance has been observed when the distance between the centers of holes 22 is preferably on the order of one hundred seventy thousandths of an inch (0.170"). Finally, it should be noted that crimping surfaces 19 are angled with respect to the majority of outer surface 14 by an angle theta that is preferably on the order of about 80°. This angled configuration aids in preventing crimping device 40 from slipping off the boss 18 during a crimping procedure. Those skilled in the art will appreciate that these dimensions and angle are preferred but other combinations of dimensions and angle would perform satisfactorily depending upon several factors, including the diameter of holes 22, the precise alloy being utilized, and other factors known in the art.

Referring now to FIG. 6, an enlarged sectioned view of implant 10 is shown in order to better illustrate the relationship between holes 22 and that portion of outer surface 14 against which cable 21 rests. It has been found that by providing a continuous cable contact surface, the stresses in cable 21 are more evenly distributed throughout the cable rather than being concentrated at certain points. This stress distribution strategy is further accomplished by contouring the outer surface 14 so that it is tangent to the cylindrical surface defining holes 22 at its ends 24. Although it is desirable that bosses 18 be machined integral to underlying plate portion 11, it is not necessary in order gain the advantage created by the stress distribution strategy. In other words, separate grommet bosses could be manufactured in accordance with the teachings of the prior art yet utilize the teachings of the present invention to create a tangential transition between the openings in the bosses to the outer surface of the bone plate in order to better distribute stress in cables 21.

Referring now to FIGS. 4, 5 and 7, a bone plate stabilization implant 110 is illustrated. Implant 110 is substantially identical to the earlier embodiment except that the shape of integrated bosses 118 is slightly different. However, like the earlier embodiment, the implant can be thought of as including a bone contact surface 113 and an outer surface 114, which includes integrated bosses 118. A plurality of openings 116 are distributed along the length of implant 110 in a manner similar to that of the earlier embodiment. A portion of these openings being compression screw holes 116 of a type known in the art. Each boss 118 includes a pair of parallel crimping holes 122 that extends substantially perpendicular to the center line 112 of implant 110. Each boss also includes a pair of crimping surfaces 119 that are angled with respect to the majority of outer surface 114 at an angle similar to that of the earlier embodiment. As can be seen in FIG. 7, 8, the pair of holes 122 are positioned, and a portion of the outer surface 114 is contoured, in order to provide a continuous cable contact surface. While this configuration better distributes stress than the structures of the prior art, it is less desired than the embodiment shown in FIG. 6 because the transition from openings 122 to outer surface 114 is continuous but not tangential as in the earlier embodiment.

Referring now to FIGS. 6–9, the advantageous features of the present invention can be easily compared to the prior art bone stabilization implants 210 and 310 shown in FIGS. 8 and 9. As can be seen, neither prior art device produces a continuous cable contact surface as in the present invention. Instead, the cables 221 and 321 of the prior art devices contact the bone stabilization implant 210 and 310, respectfully at three separate locations. Thus, a portion of the cable 222 and 322 is left unsupported between these contact points. The result being that stress is concentrated at the exit of the boss openings 224 and 324 as well as the corner contact points 223 and 325. The stress concentrations at these points will eventually result in a weakening of cables 221 and 321, with the eventual result being breakage of the cable.

Another important difference between the present invention and implants of the prior art is the integrated nature of applicant's bosses 18 and 118 to the underlying plate portion 10 and 110, respectively. In the prior art, these two features are separate parts which allows for the production of undesirable micro motion as discussed above. The bone stabilization implant 210 of FIG. 8 includes a bone plate portion 211 and a plurality of separate grommets 230 that are received in troughs 225 which are machined in the outer surface 226 of the plate. This configuration inherently permits a certain amount of micro motion of grommet 230 within trough 225.

The prior art bone stabilization implant 310 of FIG. 9 is an improvement over the device shown in FIG. 8 because the potential for undesirable micro motion is reduced. Implant 310 of FIG. 9 is of the type described in U.S. Pat. No. 5,190,545 to Corsi et al. In this prior art device, the grommets 330 include a lower portion 331 that is received in one of the screw openings machined into bone plate 311. This structure is believed to reduce the potential for micro motion over the prior art device shown in FIG. 8, but nevertheless must inherently permit some micro motion because of the required clearances between lower portion 331 of grommet 330 and the screw opening 316.

Referring now to FIG. 10, a third embodiment of a bone stabilization implant 510 is illustrated. In this embodiment, a single solid piece of stainless steel is machined to include a bone plate portion 511 and a barrel portion 512, which is suitable for use as a compression hip screw system. Implant 510 is shown attached to proximal femur bone 5. Like the earlier embodiments, plate portion 511 includes a bone contact surface 513 and an outer surface 514 that is machined to include a plurality of bosses 518. Likewise, the plurality of screw openings facilitate the use of bone screws 517 for attaching plate portion 511 to the bone. In some cases it is desirable to utilize a larger angled screw 529 in order to better secure implant 510 and any bone fragments that may exist at the fracture location. In addition to screws 517 and 529, bone plate portion 511 is secured to bone 5 using cables 521 which are wrapped around the bone and secured to bosses 518 using a crimping action of the type similar to the earlier embodiments. Barrel 512 is hollow and keyed to correspond to a flat surface 531 in lag screw 530 so that the lag screw is prevented from rotating relative to barrel 512 after the device is implanted.

FIG. 11 shows still another embodiment of a bone stabilization implant 610 according to the present invention. This implant is designed for supracondylar or "T" condylar fractures about the distal femur. Like the previous embodiment, implant 610 includes a bone plate portion 611 having a bone contact surface 613 and an outer surface 614. Implant 610 is preferably machined from a single solid piece of stainless steel to include the plate portion 611 and a barrel portion 612. Barrel portion 612 is hollow for receiving a lag screw 630 and is keyed to correspond to flat surface 631 on lag screw 630. This prevents lag screw 630 from rotating with respect to barrel 612 after the device is implanted. The device is shown attached to a distal femur bone 5.

Like the earlier embodiments, a plurality of screw holes extend between the outer surface 614 and the bone contact surface 613, and are sized to receive self-tapping cortical screws of a type known in the art. Outer surface 614 is also machined to include a plurality of bosses 618 that are distributed between the screw hole openings. In this embodiment, implant 610 is secured to the bone using lag screw 630, screw 629 and several 4.5 millimeter cortical screws 617. Also, implant 610 is further secured by the use of cables 621 that has its ends received in the holes of bosses 618, which is then crimped to clamp the ends of the cable 621 in place.

From the preceding description of the preferred embodiments, it is evident that the objects of the invention are attained. Although the invention has been described and illustrated in detail, it is to be clearly understood that the same is intended by way of illustration and example only and is not to be taken in any way that limits the scope of the invention. The spirit and scope of the invention are to limited only by the terms set forth in the claims.

I claim:

1. A bone stabilization implant comprising:

a bone plate portion having a plurality of openings extending through an outer surface and a bone contact surface and being positioned at locations along a length of said bone plate portion, and said openings being sized to receive a bone screw;

a plurality of bosses positioned at locations along said length, each of said bosses having crimping surfaces and a pair of holes therethrough that are sized to receive cable;

each of said bosses being deformable to clamp cable received in said pair of holes when said crimping surfaces are crimped; and said bone plate portion and said bosses being integral portions of a single piece of material.

2. The bone stabilization implant of claim 1 wherein a portion of said openings are compression screw holes.

3. The bone stabilization implant of claim 1 wherein each of said pair of holes is positioned and a portion of said outer surface is contoured to provide a continuous cable contact surface across a width of said bone plate portion.

4. The bone stabilization implant of claim 1 wherein a portion of said plurality of bosses are each located between a pair of said plurality of openings.

5. The bone stabilization implant of claim 1 wherein said single piece of material is a single solid piece of an implantable metallic surgical alloy.

6. The bone stabilization implant of claim 1 wherein said single piece of material is machined to include a barrel adjacent one end of said bone plate portion; and said barrel having a hole sized to receive a lag screw therethrough.

7. The bone stabilization implant of claim 6 wherein said barrel includes means for preventing relative rotation between said barrel and said lag screw received in said hole.

8. The bone stabilization implant of claim 1 wherein a portion of each of said pair of holes is defined by a cylindrical surface having ends; and a portion of said cylindrical surface is substantially tangent to said outer surface at said ends of said cylindrical surface.

9. The bone stabilization implant of claim 1 wherein said outer surface includes a pair of gripping surfaces positioned away from a majority of said outer surface.

10. A bone stabilization implant for attachment to a bone comprising:

at least one bone screw;

at least one length of cable having two ends;

a single piece of material having a bone plate portion with a length, a centerline, a bone contact surface and an outer surface;

said bone plate portion having a plurality of openings extending through said outer surface and said bone contact surface and being positioned at locations along said length, said openings being sized to receive said at least one bone screw;

a plurality of bosses positioned at locations along said length, each of said bosses having crimping surfaces and a pair of holes therethrough that are sized to receive cable;

each of said bosses being deformable to clamp cable received in said pair of holes when said crimping surfaces are crimped; and each of said pair of holes are positioned, and a portion of said outer surface is contoured, to provide a continuous cable contact surface across a width of said bone plate portion when said ends of said cable are received in said pair of holes.

11. The bone stabilization implant of claim 10 wherein said bone plate portion and said bosses are integral portions of said single piece of material.

12. The bone stabilization implant of claim 11 wherein a portion of said openings are compression screw holes.

13. The bone stabilization implant of claim 11 wherein a portion of said plurality of bosses are each located between a pair of said plurality of openings.

14. The bone stabilization implant of claim 11 wherein said single piece of material is a single solid piece of an implantable metallic surgical alloy.

15. The bone stabilization implant of claim 11 wherein said single piece of material is machined to include a barrel adjacent one end of said bone plate portion; and said barrel having a hole sized to receive a lag screw therethrough.

16. The bone stabilization implant of claim 15 wherein said barrel includes means for preventing relative rotation between said barrel and said lag screw received in said hole.

17. The bone stabilization implant of claim 10 wherein a portion of each of said pair of holes is defined by a cylindrical surface having ends; and a portion of said cylindrical surface is substantially tangent to said outer surface at said ends of said cylindrical surface.

18. The bone stabilization implant of claim 10, wherein said outer surface includes a pair of gripping surfaces positioned away from a majority of said outer surface.

19. A bone stabilization implant consisting essentially of:

a bone plate portion having a plurality of openings extending through an outer surface and a bone contact surface and being positioned at locations along a length of said bone plate portion, and said openings being sized to receive a bone screw;

a plurality of bosses positioned at locations along said length, each of said bosses having crimping surfaces and a pair of holes therethrough that are sized to receive cable;

each of said bosses being deformable to clamp cable received in said pair of holes when said crimping surfaces are crimped; and said bone plate portion and said bosses being integral portions of a single piece of material.

20. The bone stabilization implant of claim 19 wherein a portion of said openings are compression screw holes.

21. The bone stabilization implant of claim 19 wherein each of said pair of holes is positioned and a portion of said outer surface is contoured to provide a continuous cable contact surface across a width of said bone plate portion.

22. The bone stabilization implant of claim 19 wherein a portion of said plurality of bosses are each located between a pair of said plurality of openings.

23. The bone stabilization implant of claim 19 wherein said single piece of material is a single solid piece of an implantable metallic surgical alloy.

24. The bone stabilization implant of claim 19 wherein a portion of said single piece of material includes a barrel adjacent one end of said bone plate portion; and said barrel having a hole sized to receive a lag screw therethrough.

25. The bone stabilization implant of claim 19 wherein a portion of each of said pair of holes is defined by a cylindrical surface having ends; and a portion of said cylindrical surface is substantially tangent to said outer surface at said ends of said cylindrical surface.

26. The bone stabilization implant of claim 19 wherein said outer surface includes a pair of gripping surfaces positioned away from a majority of said outer surface.

* * * * *